Figure 1:
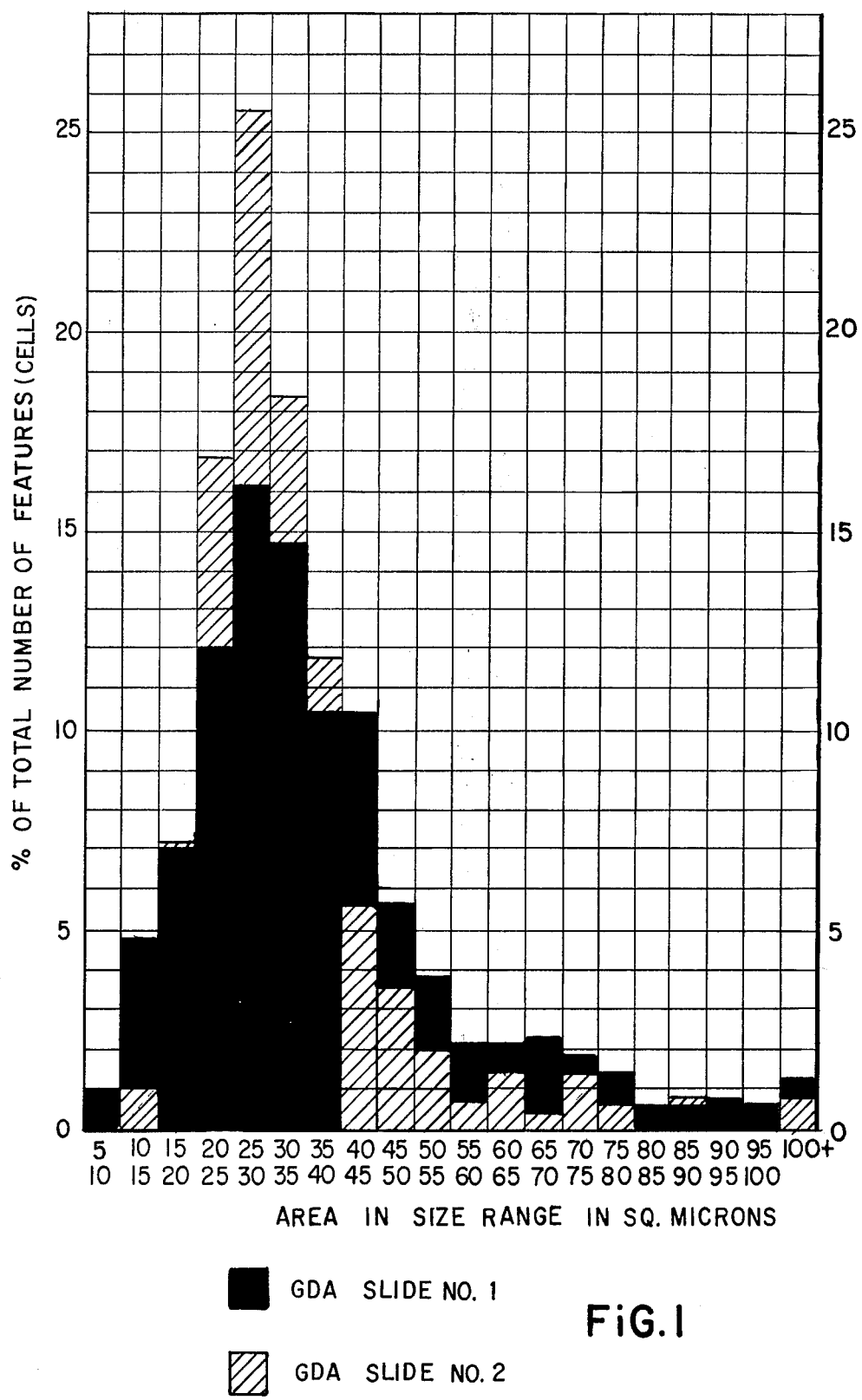
Figure 2:
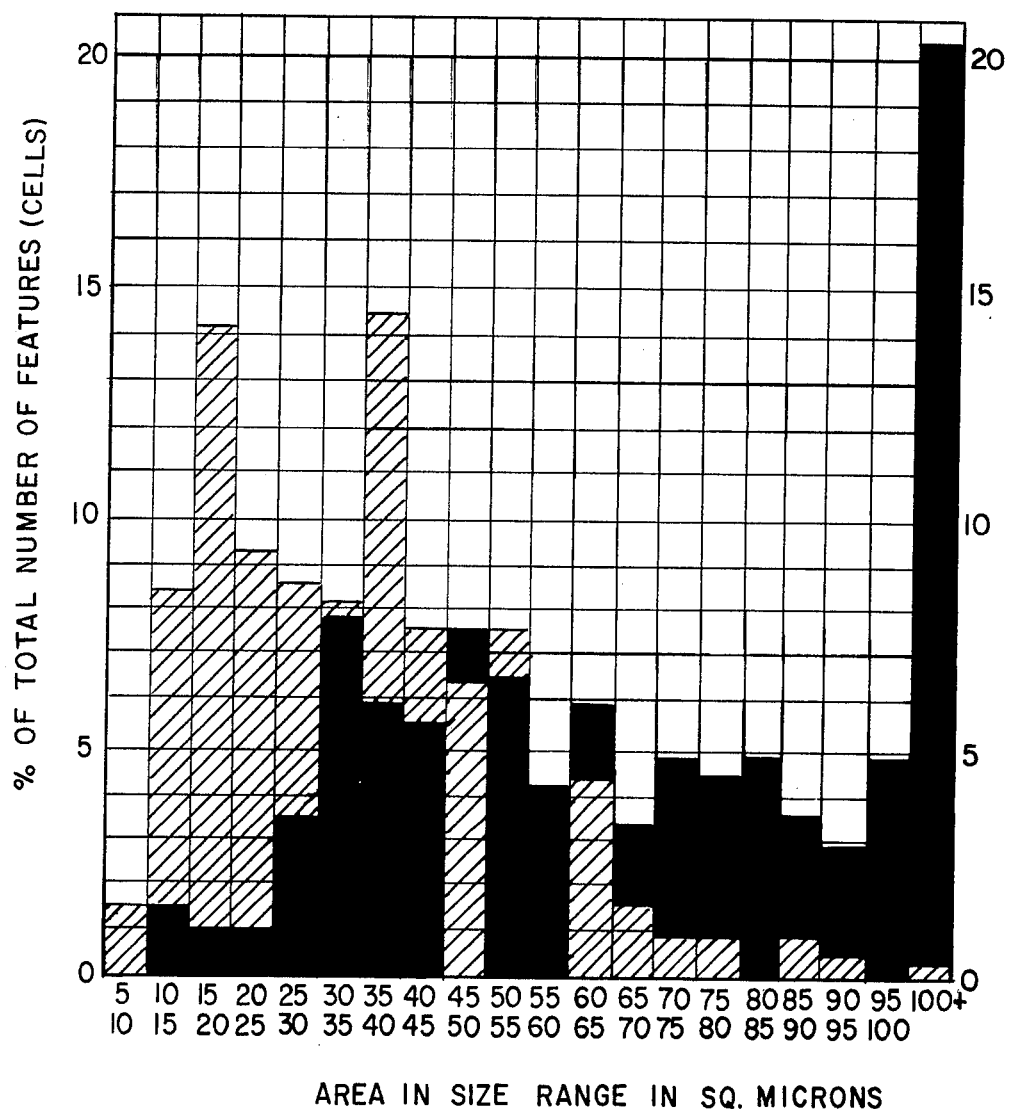

United States Patent [19]

Balassa et al.

[11] 4,212,857

[45] Jul. 15, 1980

[54] METHOD FOR STIMULATING THE PRODUCTION OF IMMUNOGLOBULIN AND TOTAL COMPLEMENT

[75] Inventors: Leslie L. Balassa, Blooming Grove; John F. Prudden, Upper Nyack, both of N.Y.

[73] Assignee: Cescarden Ltd., Goshen, N.Y.

[21] Appl. No.: 736,770

[22] Filed: Oct. 29, 1976

[51] Int. Cl.² ............................................. A61K 35/12
[52] U.S. Cl. ...................................................... 424/95
[58] Field of Search .......................................... 424/95

[56] References Cited

U.S. PATENT DOCUMENTS

| Re. 28,093 | 7/1974 | Balassa | 424/95 |
| 3,318,774 | 5/1967 | Dingwall et al. | 424/95 |
| 3,966,908 | 6/1976 | Balassa | 424/95 |

OTHER PUBLICATIONS

Merck Index, 8 ed., Merck & Co., Inc., Rahway, N.J., 1968, pp. 137 and 138.

*Primary Examiner*—Jerome D. Goldberg
*Attorney, Agent, or Firm*—Darby & Darby

[57] ABSTRACT

A method for stimulating the production of immunoglobulin and total complement in a manner by administering a liquid extract of essentially pure granulated cartilage material substantially free from adhering tissue.

7 Claims, 3 Drawing Figures

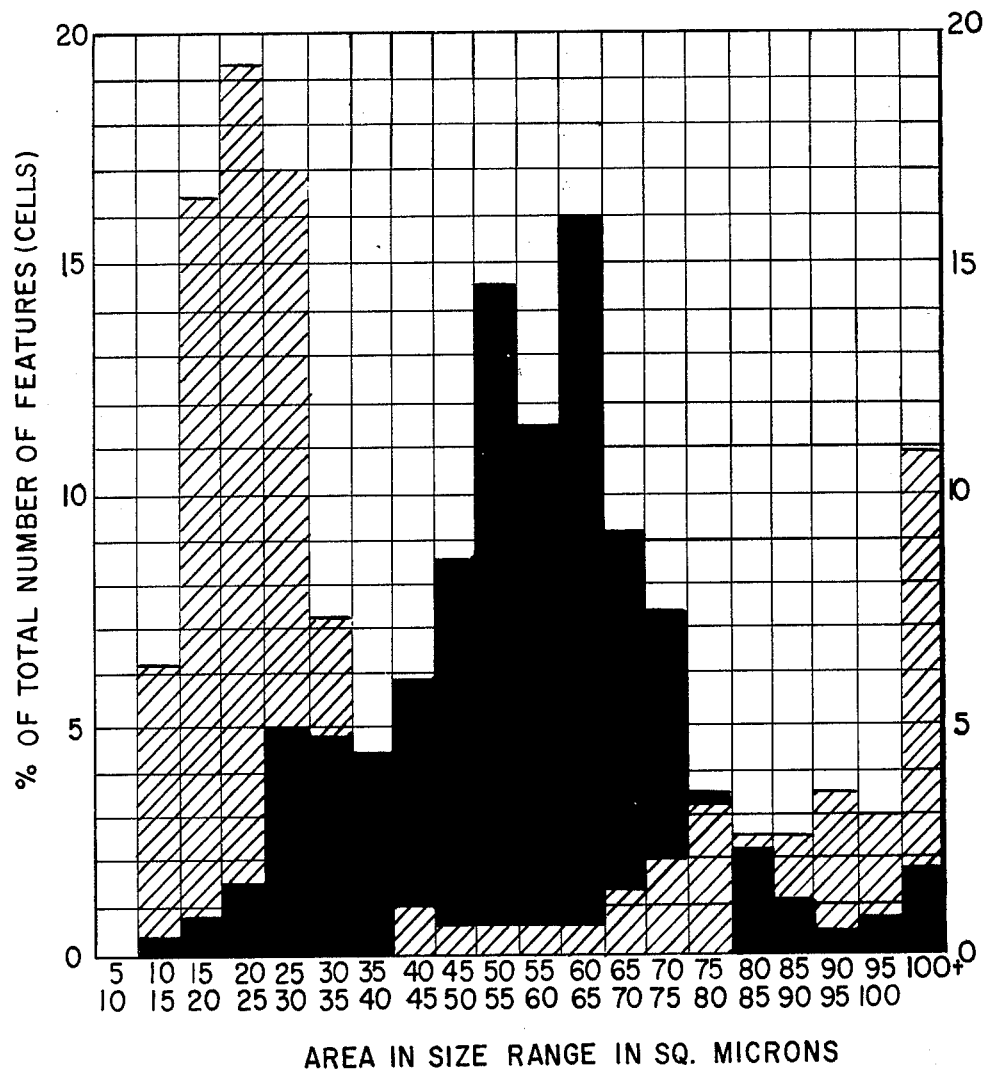

METHOD FOR STIMULATING THE PRODUCTION OF IMMUNOGLOBULIN AND TOTAL COMPLEMENT

This invention relates to a method of stimulating the production of increased titers of immunoglobulin and total complement in mammals.

It has now been unexpectedly discovered that administration of an aqueous extract of granulated animal cartilage tissue is useful to stimulate the immune system of an individual in need of such treatment and to result in enhanced levels of immunoglobulins and complement.

As used in the present specification the term "cartilage extract" refers to an aqueous extract derived from granulated animal cartilage.

U.S. Pat. No. Re. 28,093 describes the use of cartilage powder to accelerate and improve the healing of certain types of wounds. U.S. Pat. No. 3,966,908 discloses that aqueous extracts derived from granulated animal cartilage are useful in the treatment of degenerative joint diseases in mammals. Both of the preceding patents, the disclosures of which are incorporated herein by reference, teach the preparation of aqueous cartilage extracts.

The cartilage employed to prepare the aqueous extracts of the present invention is preferably derived from young cartilage, i.e. from young animals or young or newly regenerated cartilage from older animals such as reptiles or from species such as fish or shark in which cartilage remains "young" for the life of the animal. Where age is the criteria for defining "young" the cartilage is preferably derived from animals less than 6 months old. It has also been found that cartilage derived from older animals is also useful in preparing the aqueous extracts of the present invention, but that such extracts are somewhat less effective.

The raw cartilage may be prepared by any suitable means to result in a product which is essentially pure cartilage substantially free from adhering tissue which may have been removed by acid pepsin digestion or other suitable treatment, with or without mechanical assistance or otherwise.

Prior to extraction, the cartilage material is granulated. The average size of each granulated cartilage particle is not critical and successful extracts have been prepared using particles as large as 5 centimeters or more, although it has been found that more efficient extraction can be conducted when the cartilage is pulverized to a particle size below about 500 microns. The cartilage material may be pulverized using any number of techniques including ball milling, hammer milling in an inert atmosphere, pebble milling and fluid energy mill grinding.

The granulated cartilage material may be extracted according to the methods described in U.S. Pat. No. 3,400,199.

In general, cartilage extracted are obtained by the use of pharmaceutically acceptable aqueous extracting agents which dissolve the active component of the granulated animal cartilage. Thus, the extract is a product from which a substantial portion of the nonactive components have been removed and therefore has a higher concentration of activity per unit dose. Examples of suitable extraction aids include ammonia or ammonium carbonate, or such materials which on remaining in the extract would be pharmaceutically acceptable. Dialysis may be employed to remove undesired salts or other dialysable material which may be present. Examples of other extraction aids include urea, sodium citrate, disodium phosphate, trisodium phosphate, sodium formate, sodium chloride, and similar compounds or mixtures of them. In one embodiment of the invention the cartilage extract may be dialysed to separate impurities thereby yielding a product which provides enhanced activity in some circumstances.

The cartilage extract preferably used in the present invention, is an injectable dosage form of a granulated cartilage extract with isotonic saline solution. In one preferred embodiment of the invention, the isotonic saline extract is made into an injectable dosage form by dilution with sterile water to yield a sterile solution. The liquid used to extract cartilage powder for preparation of an injectable dosage unit is usually isotonic saline solution containing 0.9% NaCl (USP injectable saline), although the invention is not limited to using this material as the injectable extraction liquid. The aqueous cartilage extract may be suspended in oils such as soybean oil, corn oil, olive oil or linseed oil. The oil dispersions may be emulsified in water, forming oil in water type emulsions, or conversely, water may be emulsified in the oil dispersions forming water in oil emulsions.

The injectable cartilage extracts of the present invention contain from about 1 to about 10% and preferably about 6% cartilage extract diluted in sterile water, USP injectable saline or the like. In most instances, the sterile extract to be used for injection contains a preservative such as benzyl alcohol, or paraben and is a light brown translucent liquid that is slightly viscous at 20° C. and a a gel at 0° C. The cartilage extract may be prepared by heating the aqueous cartilage suspension for about at least approximately 15 minutes up to 24 hours or more at temperatures from about 75° C. to about 130° C., or preferably by autoclaving for 90 minutes at 15 lbs. pressure at 121° C. with all adjuvants, if any be employed. Immediately prior to administration, the injectable dosage solution can be diluted approximately 10% with 1% lidocaine (or equivalent local anesthetic) to alleviate possible discomfort.

In order to stimulate the higher titers of immunoglobulin and total complement, the sterile cartilage extract is preferably administered subcutaneously in those areas of the body possessing a readily distensible subcutaneous space (e.g., the back, anterior thorax, abdomen and anterior thighs).

Administration is carried out by injecting (either parenterally or subcutaneously) from about 1 to 75 cc. and preferably from about 25 cc to about 50 cc of the sterile cartilage extract into each of several subcutaneous sites or depots. Preferably, a total of between about 100 and 200 ccs. of cartilage extract is administered during each treatment, although smaller quantities on the order of from about 1 to about 50 cc can be administered at more frequent intervals in the interest of patient comfort. Similarly larger amounts up to 800 cc can be administered (under brief general anesthesia) in multiple depots at less frequent intervals. In view of the relatively large volumes of medication which are to be injected, the speed of injection is intentionally slow to minimize discomfort.

Each depot should contain no less than about 1 cc. nor more than about 75 cc. of the sterile cartilage extract. In most cases a subcutaneous depot containing about 50 cc. of the sterile extract has been found to provide good results.

To minimize any discomfort attributable to the relatively large volume of the subcutaneous depots, the injectable solution desireably contains about 10% by weight of lidocaine or a similar material having localized anesthetic action. Between about 4 and about 48 hours is usually required for the aqueous cartilage extract located in each depot to be absorbed into the tissues of the body and eventually into the bloodstream thereby dissipating the cartilage depot.

The effective dosage, frequency of administration and duration of treatment of the medicaments of this invention depends upon the severity of condition, the stage and individual characteristics of each host being treated. Clinical evaluations of the present invention reveal that many subjects display objective evidence of enhanced titers of immunoglobulins after receiving between about 50 to about 200 cc per week of the aqueous cartilage extract of the present invention for a period of about four weeks. The length of clinical remission varies from patient to patient depending upon the severity and extent of the disease, and the patients general physical condition. The method of the present invention was confirmed in several patients suffering from confirmed malignant growths.

This confirmation was carried out by scanning paraffin-embedded tissue biopsy sections obtained from patients at various stages of treatment with an optical scanning microscope linked to an image analyzing computer. This apparatus is available from Imanco, Ltd. Cambridge, England, as the Quantimet 720. The device incorporates a high resolution television camera (scanning 720 lines at a rate of 10 frames per second). The camera is programmed to integrate gray levels from the viewing surface with cellular morphology (e.g., optical density of nucleus and optical density of cytoplasm), as well as perimeter size of nucleus and cytoplasm sections, through a microscope and to derive an analog signal from this information. The analog signal is converted to a digital value based on gray levels in the black and white image. In the present instance, the computerized image scanning apparatus was programmed to derive an analog signal based upon nuclear area and morphology and to determine the total number of features (i.e. nuclei) within the scanning area that fell within particular nucelear size ranges. Thus, it was possible to obtain an analysis of each tissue biopsy giving the total number of cells counted, the area size range in square microns of each cell's nucleus, and the total number of cell nuclei in each size range as a percentage of the total number of cells observed by the camera. Using this information it was possible to derive a mean nuclear area for each tissue biopsy. Since it is well recognized that malignant cells generally possess larger nuclei, it was possible to determine the effect of the cartilage extracts of the present invention upon size of the nuclei. The results of the analysis are discussed in conjunction with the graphs following table IV.

Analysis of various blood fractions associated with the immune system indicates that administration of aqueous cartilage extracts according to the present invention apparently stimulates the B cells of this system and produced increased titers of various antibodies and immunoglobulins. Patients undergoing treatment with the present invention show sharply increasing levels of immunoglobulins A and M, as well as increasing titers of total complement and C3 complement. However, no effect has been discerned on T cells or macrophages. While not wishing to be bound to any particular theory of operation for the immune stimulating aspect of the present invention, we believe that its mechanism of action may be to elicit the production of antibodies which are more effective in dealing with the "foreign" antigens which have already been detected in certain cancers. The following examples illustrate the preparation of cartilage extracts which are useful as anti-tumor agents according to the present invention.

EXAMPLE I

Cartilage Pebble Mill-ground

The tracheas of healthy adult beef cattle were removed within 30 to 60 minutes after the animals were slaughtered. The tracheas were then either processed immediately with an acid-pepsin solution or they were frozen to preserve them, in which case the acid-pepsin digestion may be deferred. The tracheas, either fresh or previously frozen, were then digested for about six hours at 50° C. in an aqueous solution containing 0.6% acetic acid (U.S.P. glacial) and 0.3% pepsin (N.F. IX grade, 3500 activity). After digestion the tracheal cartilage was removed from the acid-pepsin solution, washed first with water of about 70° C. and then with water of about 25° C. until the effluent wash water showed no trace of pepsin or acetic acid. The cartilage was dried in vacuum (20 mm. mercury) at 80° C. The dried cartilage was defatted by extracting it with a solvent, such as hexane. It was then granulated. The resulting cartilage granules ranged in size from about 250 to about 500 microns.

EXAMPLE II

Cartilage obtained from the tracheas of a one month old calf was obtained by the same procedure as described in Example I and the resulting cartilage was ground to an average particle size of about 500 microns in a laboratory four quart size porcelain jar mill loaded with one inch size (average) flint pebbles in a weight ratio of 1 cartilage to 2 pebbles. Dry ice ($CO_2$) was then put on top of the mill charge. The lid of the mill was then clamped on tight and the mill rotated as is customary in the performance of a grinding operation. The grinding was carried out at about 20° C. for 96 hours. resulting cartilage granules (approx. 40-200 microns) were thoroughly admixed in aqueous isotonic saline, and the admixture heated in an autoclave at 121° C. for about 90 minutes at 15 pounds pressure to complete the extraction. The suspended matter was removed by centrifugation and the resulting tan liquid used to fill 50 ml. vials, and then sterilized in the autoclave at 121° C. for 15 minutes at 15 psi. Cartilage powder may also be obtained from cartilage sources such as pigs, lambs, goats, skeleton of sharks, rodents, crocodiles, birds, fish, etc. Reptile cartilage is particularly desirable in view of the ability of reptiles to regenerate their tissues and even their limbs. More details on the obtaining of cartilage powder from these and other sources will be found in U.S. Pat. No. Re. 28,093.

EXAMPLE III

Liquid cartilage extracts were prepared as follows:
The cartillage obtained from a one day old calf was acid-pepsin digested as in Example I, granulated to an average particle size of about 0.2 cm, and then without drying was suspended in the extracting liquid, isotonic saline solution, and then transferred into a pebble mill which was charged to 50% of its volume with flint pebbles of average size, one inch diameter. The ratio of the cartilage to extracting liquid was kept at 25:75. The liquid suspension was charged into the mill in a quantity just sufficient to fill the voids of the pebbles with the top of the pebbles barely covered by the liquid. The air was then purged from the mill with nitrogen and the mill closed. The mill was allowed to run for 6 hours between 3° C. and 4° C. which resulted in a medium fine grinding of the cartilage granules and in the simultaneous extraction of the active wound-healing agent from the cartilage.

At the end of the 6-hour cycle, the mill was emptied, the fluid paste strained free of the pebbles, the fluid transferred into a centrifuge operated at 6000 r.p.m. and at a temperature of between 3° C. After one-half hour the centrifuge was stopped and the supernatant liquid strained through a 400 mesh nylon screen. If the strained extract was cloudy, it was returned to the centrifuge and the centrifuging repeated until a clear sightly opalescent extract was obtained.

The extracts were stored at 40° C. preserved with 0.9% benzyl alcohol.

The following extracts were thus prepared:

|   | Cartilage Source | Extracting Liquid | Total Solids of Clear Extract, By Weight, Percent |
|---|---|---|---|
| a | Bovine trachea | Distilled water | 1.3 |
| b | " | Isotonic saline sol. | 5.2 |
| c | " | Ammonia (28%) 1% in water | 6.5 |
| d | " | 2% urea in water | 9.6 |
| e | " | 1% ammonium carbonate in water | 6.4 |
| f | " | 1% disodium phosphate in water | 6.6 |
| g | " | 3% ammonium carbonate in water | 7.2 |
| h | " | 1% trisodium phosphate in water | 7.6 |
| i | " | 1% sodium citrate in water | 7.0 |
| j | " | 3% sodium citrate in water | 9.2 |
| k | " | 1% sodium formate in water | 8.2 |
| l | Piglet 1 day old | Isotonic saline solution | 6.4 |
| m | " | 1% ammonia (28%) in water | 7.1 |
| n | " | 3% ammonium carbonate in water | 8.1 |
| o | " | 3% sodium citrate in water | 10.0 |
| p | Calf One day old | Isotonic saline solution | 6.2 |
| q | " | 1% ammonia (28%) in water | 7.3 |

Note:
The isotonic saline solution was prepared with distilled water and contained 0.9% NaCl.

In addition to pebble mill and fluid energy mill grinding, satisfactory powders may also be obtained by ball milling, or hammer milling in air or under an inert gas atmosphere. While ball or pebble milling the cartilage with the extracting liquid gives satisfactory results, other methods, such as mixing the cartilage powders in the liquids with a high speed, high shear, closed turbine mixer or passing the extraction mixture through a pressure homogenizer, preferably at pressures in excess of 4000 p.s.i. will also give extracts of high activity.

A group of ten patients were treated in a continuing clinical situation by parenteral administration of aqueous cartilage extracts prepared according to Example II of the present invention.

In general, the treatement involved administration of between 50 to 100 cc of aqueous cartilage extract each week. In order to obtain controlled results each individual was treated by subcutaneously injecting a sterile solution containing 6% cartilage solids in the form of a saline cartilage extract (pH 5.5) into from 2 to 4 spaced apart depots. Each depot contained from about 25 to about 50 cc of ther aqueous extract. After the initial stages of treatment, the dosage delivered at each administration and the frequency of administration was varied depending upon the individual's response to the drug as determined by immunoglobulin and complement assays, and the patient's general physical condition. The following tabulation of case studies reports on the results obtained with cartilage extract therapy.

TABLE IV

| PATIENT IDENT., AGE & SEX | THERAPY |
|---|---|
| AF<br>Age 62<br>Male<br>#1 | 100 cc aqueous cartilage extract per week administered subcutaneously for 12 months (thighs and abdomen) |
| CP<br>Age 58<br>Female<br>#2 | 100 cc Aqueous cartilage extract administered subcutaneously in thighs, abdomen or supraclavicular space each week for 12 mos. |
| FK<br>Age 66<br>Female<br>#3 | 50 cc Aqueous cartilage extract administered subcutaneously each week for 4 months, then 100 cc subcutaneously each week for 8 mos. |
| GDA<br>Age 56<br>Male<br>#4 | 50 cc of aqueous cartilage extract administered subcutaneously each week for 8 weeks, then dosage increased to 100 cc subcutaneously per week for 16 months |
| MB<br>Age 42<br>Female<br>#5 | 100 cc of aqueous cartilage extract administered subcutaneously every other day for a total of 800 cc. |
| MK<br>#6 | Administration of 100 cc of aqueous cartilage extract into two 50 cc depots subcutaneously once a week for one year |
| MM<br>Age 74<br>Male<br>#7 | Administration of 100 cc of aqueous cartilage extract subcutaneously per week for 17 months |
| MS<br>Age 72<br>Female | Dosage of 100 cc of cartilage extract subcutaneously per week in two 50 cc adjacent depots directly to |

TABLE IV-continued

| PATIENT IDENT., AGE & SEX | THERAPY |
|---|---|
| #8 | the afflicted areas including administration in the supraclavicular area, over the right anterior chest wall, and over the right deltoid-treatment continued for 2-½ years (total treatment time 4-½ years) |
| PS #9 | 100 cc of aqueous extract administered weekly into 50 cc subcutaneous depots closest to locations where high density lesions were apparent (total dose is 14,000 cc as of 9/1/76) |
| ZH Age 77 Female #10 | 100 cc of aqueous cartilage extract administered weekly via the subcutaneous route in from 2 to 4 depots in the arms, thighs, and thorax. |

In none of the preceding cases were there any instances of toxicity or abnormal liver chemistry, disturbed renal function or evidence of sensitivity attributable to the cartilage extract of the invention. Immunoglobulin and complement assays on several patients revealed increasing titers of immunoglobulins A, and M, C3 complement, and total complement.

Slides obtained at varying intervals from patients 4, 5 and 8 (in Table IV) were scanned with the Quantimet 720 apparatus and integrated to digital values by the computer. The graphs following each description summarize the data obtained from each slide.

GDA—PATIENT NO. 4 FROM TABLE IV

Slide #A of patient GDA (No. 4) was obtained from a biopsy taken about 20 weeks prior to the commencement of treatment. The mean nuclear size (area) of the cells observed was 32.5 microns. (No graph shown)

Slide #1 of patient GDA was obtained by a biopsy taken on the day before treatment commenced. It can be seen that the mean nucleus size remained the same as in slide A (approx. 32.5 microns).

GDA slide #2 was obtained from a biopsy taken approximately 8 weeks after treatment commenced. The mean size of the nuclei had decreased to 27.5 microns. This is a decrease of 16% of the mean nuclear size prior to the commencement of treatment.

PATIENT NO. 5-MB FROM TABLE IV

Slide #1 of patient No. 5 was obtained from a biopsy taken several days prior to the commencement of treatment. As determined from the computer printout obtained from the Quantimet apparatus, the mean nuclear size was 62.5 microns. In addition, a large number of nuclei having areas greater than 80 microns were observed.

Slide #2 was obtained from a biopsy taken 18 days after the commencement of treatment. The mean nuclear size decreased to 33.0 microns, a decrease of 47%. Very few cells were observed in which the nuclei had an area greater than 75 microns.

PATIENT NO. 8—MS—FROM TABLE IV

MS slide #1 was obtained prior to starting administration of 100 ccs. of cartilage extract per week. The mean size of the cell nuclei was approximately 55 microns.

MS slide #2 was obtained from a biopsy taken about 10 months after slide #1. During this period the patient had been receiving 100 ccs. of aqueous cartilage extract subcutaneously each week in two 50 cc depots. The mean nuclear size on slide #2 declined to 25.0 microns, a decrease of 55%.

All of the foregoing image scanning analyses confirm that administration of the cartilage extracts of the present invention leads to a decrease in the nuclear area of cells.

Salts other than NaCl may provide more effective extraction, as shown in Example II. An inert atmosphere during the extraction results in extracts of greater potency than when the extraction is carried out in the presence of oxygen. However, since the presence of oxygen during processing has in some instances completely inactivated extracts of the cartilages herein shown otherwise to be vastly superior, the use of well-known, pharmaceutically acceptable non-toxic antioxidants such as ascorbic acid or its salts, or vitamin A may permit carrying out the extraction in the presence of air without serious loss of potency.

What is claimed is:

1. The method of stimulating the production of increased titers of immunoglobulin and total complement which comprises administering to a patient in need of such treatment an effective amount for stimulating immunoglobulin and total complement of an aqueous solution consisting essentially of at least the aqueous soluble portion of defatted and essentially pure granulated cartilage material substantially free from adhering tissue, said cartilage being derived from a cartilage bearing animal or fish.

2. The method of claim 1 which comprises subcutaneously administering said cartilage to said patient.

3. The method of claim 2 wherein said effective amount is delivered in a plurality of individual treatments.

4. The method of claim 3 which comprises administering to said patient from 1 to about 200 cc of said cartilage extract during each of said individual treatments.

5. The method according to claim 1 which comprises subcutaneously administering said extract to said human in a distensible area of the body.

6. The method according to claim 1 wherein said cartilage is derived from a reptile.

7. A method for stimulating the production of C3 serum complement in a human which comprises subcutaneously administering to a human in need of such treatment an effective amount for stimulating C3 complement of an aqueous extract consisting essentially of at least the aqueous soluble portion of essentially pure granulated cartilage material substantially free from adhering tissue, said cartilage extract having been dialyzed prior to administration to said human and said cartilage being derived from a cartilage bearing animal or fish.

* * * * *

UNITED STATES PATENT AND TRADEMARK OFFICE
CERTIFICATE OF CORRECTION

PATENT NO. : 4,212,857
DATED : July 15, 1980
INVENTOR(S) : Leslie L. Balassa, John F. Prudden It is certified that error appears in the above-identified patent and that said Letters Patent are hereby corrected as shown below:

Correct the Title page, line [73] Assignee: "Cescarden Ltd.", Goshen, N.Y.

to -- Lescarden Ltd. --.

Signed and Sealed this

Twenty-fourth Day of August 1982

|SEAL|

Attest:

GERALD J. MOSSINGHOFF

Attesting Officer

Commissioner of Patents and Trademarks